(12) United States Patent
Xie et al.

(10) Patent No.: US 11,101,029 B2
(45) Date of Patent: Aug. 24, 2021

(54) SYSTEMS AND METHODS FOR PREDICTING MEDICATIONS TO PRESCRIBE TO A PATIENT BASED ON MACHINE LEARNING

(71) Applicant: Petuum Inc., Pittsburgh, PA (US)

(72) Inventors: Pengtao Xie, Pittsburgh, PA (US); Eric Xing, Pittsburgh, PA (US)

(73) Assignee: PETUUM INC., Pittsburgh, PA (US)

( * ) Notice: Subject to any disclaimer, the term of this patent is extended or adjusted under 35 U.S.C. 154(b) by 132 days.

(21) Appl. No.: 16/207,114

(22) Filed: Dec. 1, 2018

(65) Prior Publication Data

US 2020/0027539 A1 Jan. 23, 2020

Related U.S. Application Data

(60) Provisional application No. 62/699,385, filed on Jul. 17, 2018, provisional application No. 62/756,024, filed on Nov. 5, 2018.

(51) Int. Cl.
*G16H 20/10* (2018.01)
*G16H 10/60* (2018.01)
(Continued)

(52) U.S. Cl.
CPC .............. *G16H 20/10* (2018.01); *G06F 16/36* (2019.01); *G06F 40/284* (2020.01); *G06K 9/46* (2013.01);
(Continued)

(58) Field of Classification Search
CPC ........ G16H 20/10; G16H 15/00; G16H 30/40; G16H 70/60; G16H 50/20; G16H 10/60;
(Continued)

(56) References Cited

U.S. PATENT DOCUMENTS 10,224,119 B1 3/2019 Heinrich et al.
10,496,884 B1 12/2019 Nguyen et al.
(Continued)

FOREIGN PATENT DOCUMENTS

JP 2009-295717 A * 12/2009 ............. G16H 10/60

OTHER PUBLICATIONS

Pengtao Xie, Jun Zhu, Eric P. Xing, Diversity-Promoting Bayesian Learning of Latent Variable Models, International Conference on Machine Learning, vol. 48, pp. 1-10 (Year: 2016).*
(Continued)

*Primary Examiner* — Linh Giang Le

(57) ABSTRACT

A system for predicting medications to prescribe to a patient includes a text encoding module and a medication prediction module. The text encoding module is configured to obtain a clinical-information vector from clinical information of the patient. The medication prediction module configured to apply a machine-learned medication-prediction algorithm to the clinical-information vector to select a subset of medications to prescribe to the patient. The machine-learned medication-prediction algorithm is designed with a diversity-promoting regularization model, and is configured to simultaneously consider correlations among different medications and dependencies between patient information and medications when selecting a subset of medications to prescribe to the patient.

11 Claims, 5 Drawing Sheets

(51) Int. Cl.
| | |
|---|---|
| *G06N 20/00* | (2019.01) |
| *G16B 40/00* | (2019.01) |
| *G16H 50/20* | (2018.01) |
| *G16H 70/60* | (2018.01) |
| *G06N 3/08* | (2006.01) |
| *G16H 15/00* | (2018.01) |
| *G16H 30/40* | (2018.01) |
| *G06K 9/46* | (2006.01) |
| *G06K 9/62* | (2006.01) |
| *G06T 7/00* | (2017.01) |
| *G06F 16/36* | (2019.01) |
| *H04L 29/08* | (2006.01) |
| *G06F 40/284* | (2020.01) |
| *G16H 50/70* | (2018.01) |
| *G16B 50/00* | (2019.01) |
| *G06K 9/72* | (2006.01) |

(52) U.S. Cl.
CPC ............ *G06K 9/6228* (2013.01); *G06N 3/08* (2013.01); *G06N 20/00* (2019.01); *G06T 7/0012* (2013.01); *G16B 40/00* (2019.02); *G16H 10/60* (2018.01); *G16H 15/00* (2018.01); *G16H 30/40* (2018.01); *G16H 50/20* (2018.01); *G16H 70/60* (2018.01); *H04L 67/104* (2013.01); *G06K 9/628* (2013.01); *G06K 9/726* (2013.01); *G06K 2209/05* (2013.01); *G06T 2207/20081* (2013.01); *G06T 2207/20084* (2013.01); *G16B 50/00* (2019.02); *G16H 50/70* (2018.01)

(58) Field of Classification Search
CPC ........ G16H 50/70; G06K 9/46; G06K 9/6228; G06K 9/628; G06K 9/726; G06K 2209/05; G06T 7/0012; G06T 2207/20081; G06T 2207/20084; G06N 3/08; G06N 20/00; G16B 40/00; G16B 50/00
See application file for complete search history.

(56) References Cited

U.S. PATENT DOCUMENTS

| | | |
|---|---|---|
| 2005/0071194 A1 | 3/2005 | Bormann et al. |
| 2006/0253441 A1 | 11/2006 | Nelson |
| 2008/0085307 A1* | 4/2008 | Sundharadas ........ A61K 9/4808 424/464 |
| 2011/0119212 A1* | 5/2011 | De Bruin ................ A61B 5/00 706/12 |
| 2012/0330958 A1 | 12/2012 | Xu et al. |
| 2014/0089000 A1 | 3/2014 | Takata et al. |
| 2017/0154163 A1* | 6/2017 | Jerby Arnon .......... G16H 50/50 |
| 2017/0228433 A1* | 8/2017 | Gartrell ................. G06N 7/005 |
| 2017/0371623 A1 | 12/2017 | Ross |
| 2018/0137244 A1 | 5/2018 | Sorenson et al. |
| 2018/0285679 A1* | 10/2018 | Amitay .................. G06T 5/007 |
| 2019/0035496 A1* | 1/2019 | Netzer .................. G16H 50/20 |
| 2019/0114304 A1 | 4/2019 | Oliveira et al. |
| 2019/0392547 A1 | 12/2019 | Katouzian et al. |
| 2020/0013487 A1* | 1/2020 | Luo ........... G16H 20/10 |
| 2020/0219609 A1 | 7/2020 | Harte |
| 2020/0366495 A1 | 11/2020 | Mahoney |

OTHER PUBLICATIONS

Gibbs sampling, May 2018, Wikipedia (Year: 2018).
Shai Avidan, Joint Feature-basis subset selection, 2004, IEEE Computer Society (Year: 2004).

* cited by examiner

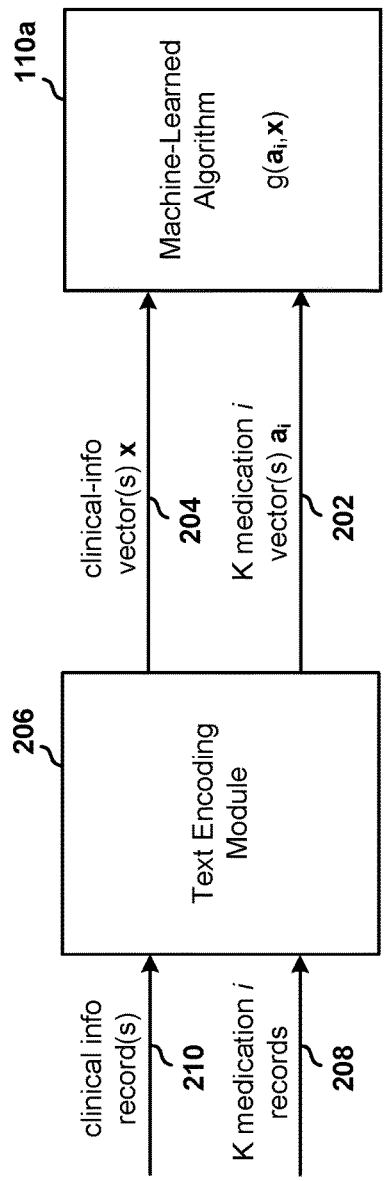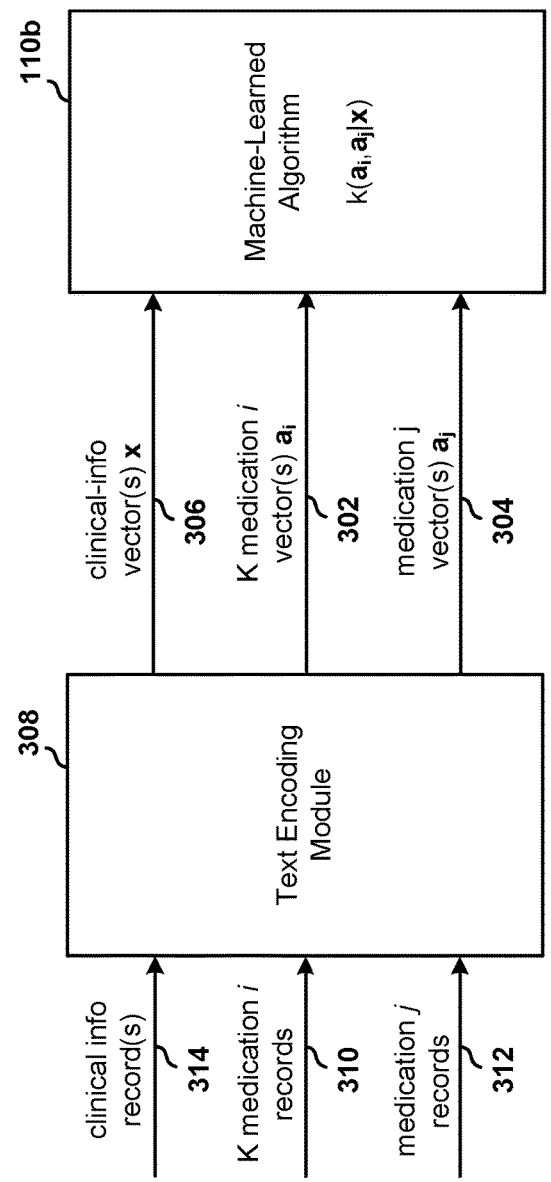

SYSTEMS AND METHODS FOR PREDICTING MEDICATIONS TO PRESCRIBE TO A PATIENT BASED ON MACHINE LEARNING

CROSS-REFERENCE TO RELATED APPLICATION(S)

This application claims the benefit of and priority to 1) U.S. Provisional Patent Application Ser. No. 62/699,385, filed Jul. 17, 2018, for "Diversity-Promoting and Large-Scale Machine Learning for Healthcare", and 2) U.S. Provisional Patent Application Ser. No. 62/756,024, filed Nov. 5, 2018, for "Diversity-Promoting and Large-Scale Machine Learning for Healthcare", the entire disclosures of which are incorporated herein by references.

This application has subject matter in common with: 1) U.S. patent application Ser. No. 16/038,895, filed Jul. 18, 2018, for "A Machine Learning System for Measuring Patient Similarity", 2) U.S. patent application Ser. No. 15/946,482, filed Apr. 5, 2018, for "A Machine Learning System for Disease, Patient, and Drug Co-Embedding, and Multi-Drug Recommendation", 3) U.S. patent application Ser. No. 16/207,115 filed Dec. 1, 2018, for "Systems and Methods for Medical Topic Discovery Based on Large-Scale Machine Learning", 4) U.S. patent application Ser. No. 16/207,117, filed Dec. 1, 2018, for "Systems and Methods for Automatically Tagging Concepts to, and Generating Text Reports for, Medical Images Based on Machine Learning", 5) U.S. patent application Ser. No. 16/207,119, filed Dec. 1, 2018, for "Systems and Methods for Automatically Generating International Classification of Disease Codes for a Patient Based on Machine Learning", the entire disclosures of which are incorporated herein by reference, and the entire disclosures of which are incorporated herein by reference.

TECHNICAL FIELD

The present invention generally relates to machine learning for healthcare, and more particularly, to systems and methods that apply machine learning algorithms to patient information obtained at admission to predict one or more medications to be prescribed to the patient at discharge.

BACKGROUND

With the widespread adoption of electronic health records (EHR) systems, and the rapid development of new technologies such as high-throughput medical imaging devices, low-cost genome profiling systems, networked and even wearable sensors, mobile applications, and rich accumulation of medical knowledge/discoveries in databases, a tsunami of medical and healthcare data has emerged. It was estimated that 153 exabytes (one exabyte equals one billion gigabytes) of healthcare data were produced in 2013. In 2020, an estimated 2314 exabytes will be produced. From 2013 to 2020, an overall rate of increase is at least 48 percent annually.

In addition to the sheer volume, the complexity of healthcare data is also overwhelming. Such data includes clinical notes, medical images, lab values, vital signs, etc., coming from multiple heterogeneous modalities including texts, images, tabular data, time series, graph and so on. The rich clinical data is becoming an increasingly important source of holistic and detailed information for both healthcare providers and receivers. Collectively analyzing and digesting these rich information generated from multiple sources; uncovering the health implications, risk factors, and mechanisms underlying the heterogeneous and noisy data records at both individual patient and whole population levels; making clinical decisions including diagnosis, triage, and treatment thereupon, are now routine activities expected to be conducted by medical professionals including physicians, nurses, pharmacists and so on.

As the amount and complexity of medical data are rapidly growing, these activities are becoming increasingly more difficult for human experts. The information overload makes medical analytics and decisions-making time consuming, error-prone, suboptimal, and less-transparent. As a result, physicians, patients, and hospitals suffer a number of pain points, quality-wise and efficiency-wise. For example, in terms of quality, 250,000 Americans die each year from medical errors, which has become the third leading cause of death in the United States. Twelve million Americans are misdiagnosed each year. Preventable medication errors impact more than 7 million patients and cost almost $21 billion annually. Fifteen to twenty-five percent of patients are readmitted within 30 days and readmissions are costly (e.g., $41.3 billion in 2011). In terms of inefficiency, patients wait on average 6 hours in emergency rooms. Nearly 400,000 patients wait 24 hours or more. Physicians spend only 27 percent of their office day on direct clinical face time with patients. The U.S. healthcare system wastes $750 billion annually due to unnecessary services, inefficient care delivery, excess administrative costs, etc.

The advancement of machine learning (ML) technology opens up opportunities for next generation computer-aided medical data analysis and data-driven clinical decision making, where machine learning algorithms and systems can be developed to automatically and collectively digest massive medical data such as electronic health records, images, behavioral data, and the genome, to make data-driven and intelligent diagnostic predictions. An ML system can automatically analyze multiple sources of information with rich structure; uncover the medically meaningful hidden concepts from low-level records to aid medical professionals to easily and concisely understand the medical data; and create a compact set of informative diagnostic procedures and treatment courses and make healthcare recommendations thereupon.

It is therefore desirable to leverage the power of machine learning in automatically distilling insights from large-scale heterogeneous data for automatic smart data-driven medical predictions, recommendations, and decision-making, to assist physicians and hospitals in improving the quality and efficiency of healthcare. It is further desirable to have machine learning algorithms and systems that turn the raw clinical data into actionable insights for clinical applications. One such clinical application relates to predicting medications for a patient.

When applying machine learning to healthcare application, several fundamental issues may arise, including:

1) How to better capture infrequent patterns: At the core of ML-based healthcare is to discover the latent patterns (e.g., topics in clinical notes, disease subtypes, phenotypes) underlying the observed clinical data. Under many circumstances, the frequency of patterns is highly imbalanced. Some patterns have very high frequency while others occur less frequently. Existing ML models lack the capability of capturing infrequent patterns. Known convolutional neural network do not perform well on infrequent patterns. Such a deficiency of existing models possibly results from the design of their objective function used for training. For example, a maximum likelihood estimator would reward itself by modeling the frequent patterns well as they are the major contributors to the likelihood function. On the other hand, infrequent patterns contribute much less to the likelihood, thereby it is not very rewarding to model them well and they tend to be ignored. Infrequent patterns are of crucial importance in clinical settings. For example, many infrequent diseases are life-threatening. It is critical to capture them.

2) How to alleviate overfitting: In certain clinical applications, the number of medical records available for training is limited. For example, when training a diagnostic model for an infrequent disease, typically there is no access to a sufficiently large number of patient cases due to the rareness of this disease. Under such circumstances, overfitting easily happens, wherein the trained model works well on the training data but generalizes poorly on unseen patients. It is critical to alleviate overfitting.

3) How to improve interpretability: Being interpretable and transparent is a must for an ML model to be willingly used by human physicians. Oftentimes, the patterns extracted by existing ML methods have a lot of redundancy and overlap, which are ambiguous and difficult to interpret. For example, in computational phenotyping from EHRs, it is observed that the learned phenotypes by the standard matrix and tensor factorization algorithms have much overlap, causing confusion such as two similar treatment plans are learned for the same type of disease. It is necessary to make the learned patterns distinct and interpretable.

4) How to compress model size without sacrificing modeling power: In clinical practice, making a timely decision is crucial for improving patient outcome. To achieve time efficiency, the size (specifically, the number of weight parameters) of ML models needs to be kept small. However, reducing the model size, which accordingly reduces the capacity and expressivity of this model, typically sacrifice modeling power and performance. It is technically appealing but challenging to compress model size without losing performance.

5) How to efficiently learn large-scale models: In certain healthcare applications, both the model size and data size are large, incurring substantial computation overhead that exceeds the capacity of a single machine. It is necessary to design and build distributed systems to efficiently train such models.

For a newly admitted patient, it is important to predict the medications prescribed to the patient at discharge time based on the information available at admission time. A successful prediction of discharge medications provides physicians with guidance on what type of medication regimen to plan for and what possible changes to an initial medication may occur during an inpatient stay. Specifically, in an inpatient setting, patients are admitted on their home medications and due to various reasons, including the cause for admission, the condition of the patient, diagnosis, and other co-morbidities, the patient's medications are changed throughout the inpatient stay and can be different at the time of discharge. For example, a chronic kidney disease patient with chronic heart failure and hypertension could be admitted for a heart failure exacerbation and then require changes to his anti-hypertensive medication. In this case, it would be helpful for the physician to understand what medications are better to add or remove through analysis of past cases given that in those situations one medication can improve one disease at the cost of exacerbating another. It may be difficult for human physicians to balance the pros and cons in that situation.

A machine learned approach that takes advantage of past case histories involving the prescribing of medications may help human physicians to predict discharge medications more accurately and timely. Several issues, however, may make this approach challenging. First, information available upon admission is mostly documented in unstructured clinical notes or admission notes, such as past medical history, family and social history, allergies, etc. Compared with structured information such as labs and vital signs, the free-form texts are more difficult to process and to understand for machines. The notes contain synonyms, abbreviations, and misspellings. Distilling semantic patterns from such unstructured and noisy texts is very challenging.

Second, a typical pharmacological treatment usually involves multi-medication therapy, where medications are prescribed in combination because they have been shown in clinical guidelines or medical consensus to have a certain impact on mortality/disease progression when used together. For example, for those patients who have had a recent stroke while already on aspirin, dual antiplatelet therapy with aspirin and clopidogrel will be recommended for future stroke prevention. How to automatically discover and leverage such pharmacological correlations among medications is crucial for more accurate multiple-medication prediction and is highly non-trivial, as it requires consideration of the interaction between medications.

SUMMARY

In one aspect of the disclosure, a method of predicting medications to prescribe to a patient includes obtaining a clinical-information vector from clinical information of the patient, and applying a machine-learned medication-prediction algorithm to the clinical-information vector to select a subset of medications to prescribe to the patient. The machine-learned medication-prediction algorithm is designed with a diversity-promoting regularization model, and is configured to simultaneously consider correlations among different medications and dependencies between patient information and medications when selecting a subset of medications to prescribe to the patient.

In another aspect of the disclosure, a system for predicting medications to prescribe to a patient includes a text encoding module and a medication prediction module. The text encoding module is configured to obtain a clinical-information vector from clinical information of the patient. The medication prediction module configured to apply a machine-learned medication-prediction algorithm to the clinical-information vector to select a subset of medications to prescribe to the patient. The machine-learned medication-prediction algorithm is designed with a diversity-promoting regularization model, and is configured to simultaneously consider correlations among different medications and dependencies between patient information and medications when selecting a subset of medications to prescribe to the patient.

It is understood that other aspects of methods and systems will become readily apparent to those skilled in the art from the following detailed description, wherein various aspects are shown and described by way of illustration.

BRIEF DESCRIPTION OF THE DRAWINGS

Various aspects of apparatuses and methods will now be presented in the detailed description by way of example, and not by way of limitation, with reference to the accompanying drawings, wherein:

FIG. 2 is a block diagram of a design for a first version of the machine-learned algorithm of FIG. 1.

FIG. 3 is a block diagram of a design for a second version of the machine-learned algorithm of FIG. 1.

DETAILED DESCRIPTION

Disclosed herein is a medication prediction system for predicting medications to prescribe to a patient, including for example, medications that a caregiver may prescribe when a patient is discharged from a care facility. The prediction of discharge medications may be formulated as a subset selection problem. Given clinical information for a patient and information on a plurality K of candidate medications Y={1, . . . , K}, the system disclosed herein predicts a subset S⊆Y of medications that are most likely to be prescribed to the patient as discharge. Some of the concepts and features described herein are included in Diversity-promoting and Large-scale Machine Learning for Healthcare, a thesis submitted by Pengtao Xie in August 2018 to the Machine Learning Department, School of Computer Science, Carnegie Mellon University, which is hereby incorporated by reference in its entirety.

The predictive function of the system results in the identification of a subset S of medications, referred to herein as "predicted medications," where each medication in the set is highly relevant to the patient's clinical condition x. In one configuration, the predictive function of the system also results in the identification of a subset S of medications, where the relations among the medications in the subset, including co-occurrence, adversarial interaction, and synergistic interaction, are accounted for to eliminate clinically-inconsistent medications.

The medication prediction system is configured to receive inputs of clinical information of a patient and to generate an output predicting one or more medications to be prescribed to the patient. The medication prediction system includes one or more machine-learned algorithms that model dependencies between patient information and medications, and that model correlations among medications. One or more of these models may involve a diversity-promoting distance metric learning model. For example, the machine-learned algorithm that correlates medications may be configured to learn representations of the medication records of numerous medications, compute similarities of the representations in a latent space, and generate a score that indicates similarities among the medications. The use of a diversity-promoting distance metric learning model is beneficial in that such models measure similarity in a way that ensures the capture of both frequently prescribed and infrequently prescribed medications with similar characteristics.

Figure 1:
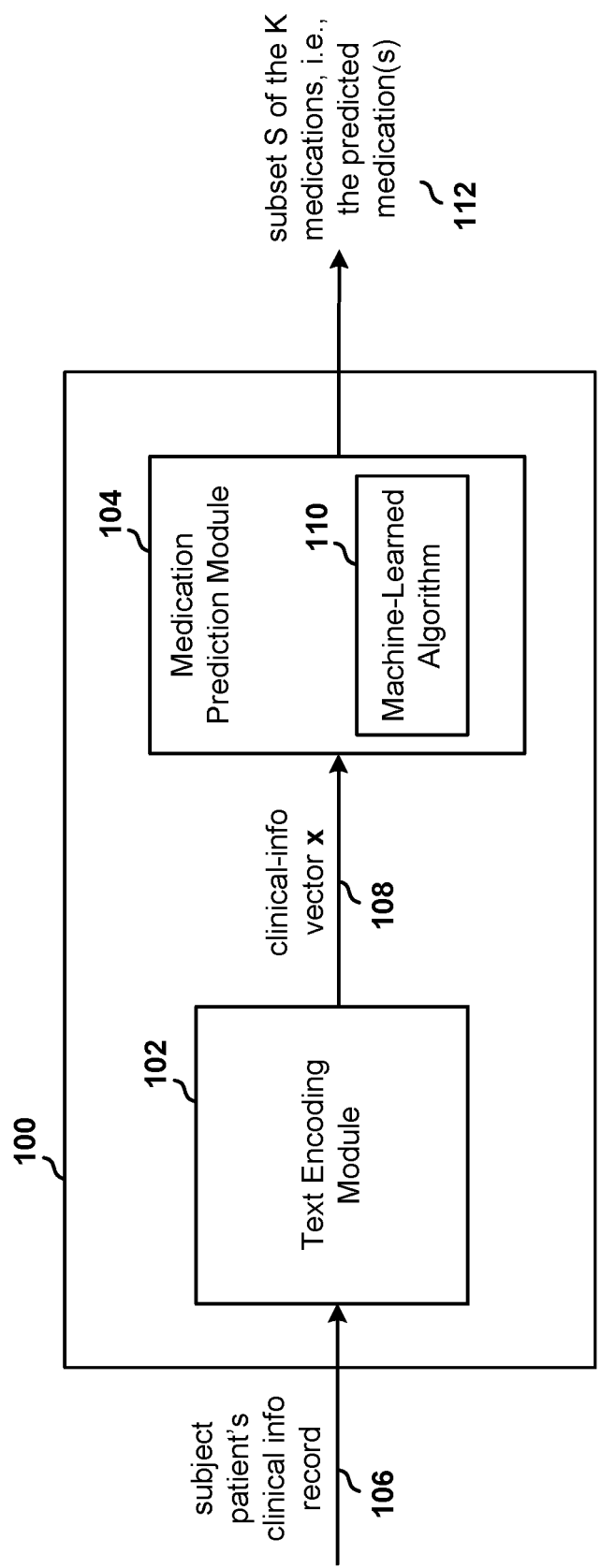
FIG. 1 is a block diagram of a system for predicting medications to prescribe to a patient using a machine-learned algorithm.

With reference to FIG. 1, in one configuration, a medication prediction system 100 includes a text encoding module 102 and a medication prediction module 104. The text encoding module 102 is configured to receive a subject patient's record of clinical information 106 and to produce a representation of the clinical information as a clinical-information vector x 108. The medication prediction module 104 receives the clinical information as the clinical-information vector x 108 and applies a previously-trained machine-learned algorithm 110 to the vector x and outputs a list of predicted medications 112.

Regarding the text encoding module 102, it is configured to extract information from the clinical record, and derive the clinical-information vector x 108 from the extracted information. The record of clinical information 106 may be hand written admission notes or printed records identifying one or more conditions of the patient. The conditions or extracted information may include, for example, one or more of the patient's current medication, vital signs, symptoms, laboratory results, past medical history, family history, social history, and allergies.

With reference to FIG. 2, in one embodiment, a machine-learned algorithm 110a for use in the medication prediction module 104 is previously trained in accordance with a training set K of medication i vectors $a_i$ 202, where $\{a_i\}_{i=1}^{K}$ and a training set of clinical information vectors x 204 to associate clinical information with medications. For example, the machine-learned algorithm 110 may define score functions g($a_i$, x) that measure the dependency between a piece of clinical information x and a medication i.

The training set K of medication i vectors $a_i$ 202 and the training set of clinical information vectors x 204 used to train the machine-learned algorithm 110, are obtained using a text encoding module 206. In one embodiment, the text encoding module 206 is configured with the same architecture and parameters as the text encoding module 102 in FIG. 1 that is used to derive a subject patient's clinical-information vector x 108.

The text encoding module 206 is configured to receive a medication record 208 for each medication i in the set of K medications, and to produce a representation of the medical information as a medication i vector $a_i$ 202. The medication records 208 may be in the form of professional medical articles that describe various aspects of a medication, including its clinical applications, e.g., what conditions/diseases the medication can treat, and its side effects, dosage, and so on. The text encoding module 206 is configured to extract information from the medication records it receives, and derive the medication i vector $a_i$ 202 from the extracted information.

Similarly, the text encoding module 206 is configured to receive a clinical information records 210, and to produce a representation of the clinical information as a clinical information vector x 204. The clinical information records 210 may be hand written admission notes or printed records identifying one or more conditions of the patient. The conditions may include, for example, one or more of the patient's current medication, vital signs, symptoms, laboratory results, past medical history, family history, social history, and allergies.

Returning to FIG. 1, with the trained machine-learned algorithm 110a at hand, the medication prediction module 104 applies the algorithm to the subject patient's clinical-information vector x 108 to identify a subset S 112 of the set of K medications for prescribing to the patient. To this end, the trained machine-learned algorithm 110a derives a score function g ($a_i$, x) that provides a measure of the dependency between the subject patient's clinical information x and the medication i in the set of K medications. The score function of each identified medication may be processed against a threshold score to determine whether the medication is included in the set of predicted medications 112 to be output by the medication prediction module 104.

With reference to FIG. 3, in another embodiment, a machine-learned algorithm 110b for use in the medication prediction module 104 is previously trained in accordance with a training set K of medication i vectors $a_i$ 302, where $\{a_i\}_{i=1}^K$, a training set of medication j vectors 304, and a training set of clinical information vectors x 306 to associate clinical information with medications. For example, the machine-learned algorithm 110 may define score functions $k(a_i, a_j|x)$ that measure the correlation between different medications i and j and the dependency between a piece of clinical information x and correlated medications i and j.

The training set K of medication i vectors $a_i$ 302, the training set of medication j vectors 304, and the training set of clinical information vectors x 306 used to train the machine-learned algorithm 110, are obtained using a text encoding module 308. In one embodiment, the text encoding module 308 is configured with the same architecture and parameters as the text encoding module 102 in FIG. 1.

The text encoding module 308 is configured to receive a medication record 310 for each medication i in the set of K medications, and to produce a representation of the medical information as a medication i vector $a_i$ 302. Likewise, the text encoding module 308 is configured to receive a medication record 312 for each medication j, and to produce a representation of the medical information as a medication j vector $a_j$ 304. The medication records 310, 312 may be in the form of professional medical articles that describe various aspects of a medication, including its clinical applications, e.g., what conditions/diseases the medication can treat, and its side effects, dosage, and so on. Similarly, the text encoding module 308 is configured to receive a clinical information records 314, and to produce a representation of the clinical information as a clinical information vector x 306. The clinical information records 314 may be hand written admission notes or printed records identifying one or more conditions of the patient. The conditions may include, for example, one or more of the patient's current medication, vital signs, symptoms, laboratory results, past medical history, family history, social history, and allergies.

Returning to FIG. 1, with the trained machine-learned algorithm 110b at hand, the medication prediction module 104 applies the algorithm to the subject patient's clinical-information vector x 108 to identify a subset S 112 of the set of K medications for prescribing to the patient. To this end, the trained machine-learned algorithm 110b derives a score function $k(a_i, a_j|x)$ that provides a measure of the dependency between the subject patient's clinical information x and correlated medications i and j. The score function of each identified medication may be processed against a threshold score to determine whether the medication is included in the set of predicted medications 112 to be output by the medication prediction module 104.

Figure 4:
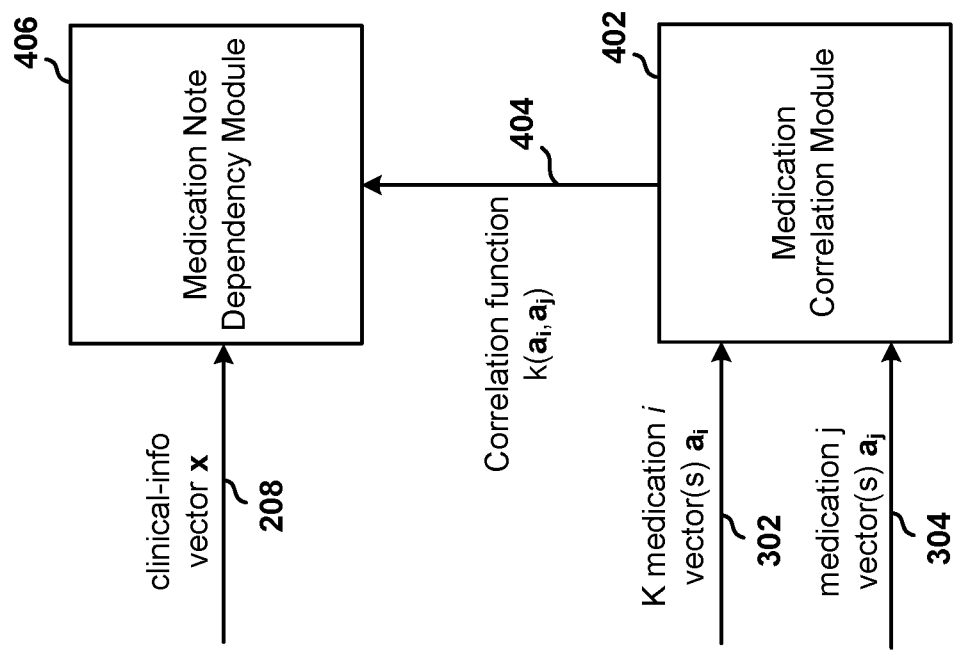
FIG. 4 is a detailed block diagram of a design for the second version of the machine-learned algorithm of FIG. 3 that includes a medication correlation module and a medication note dependency module.
Figure 5:
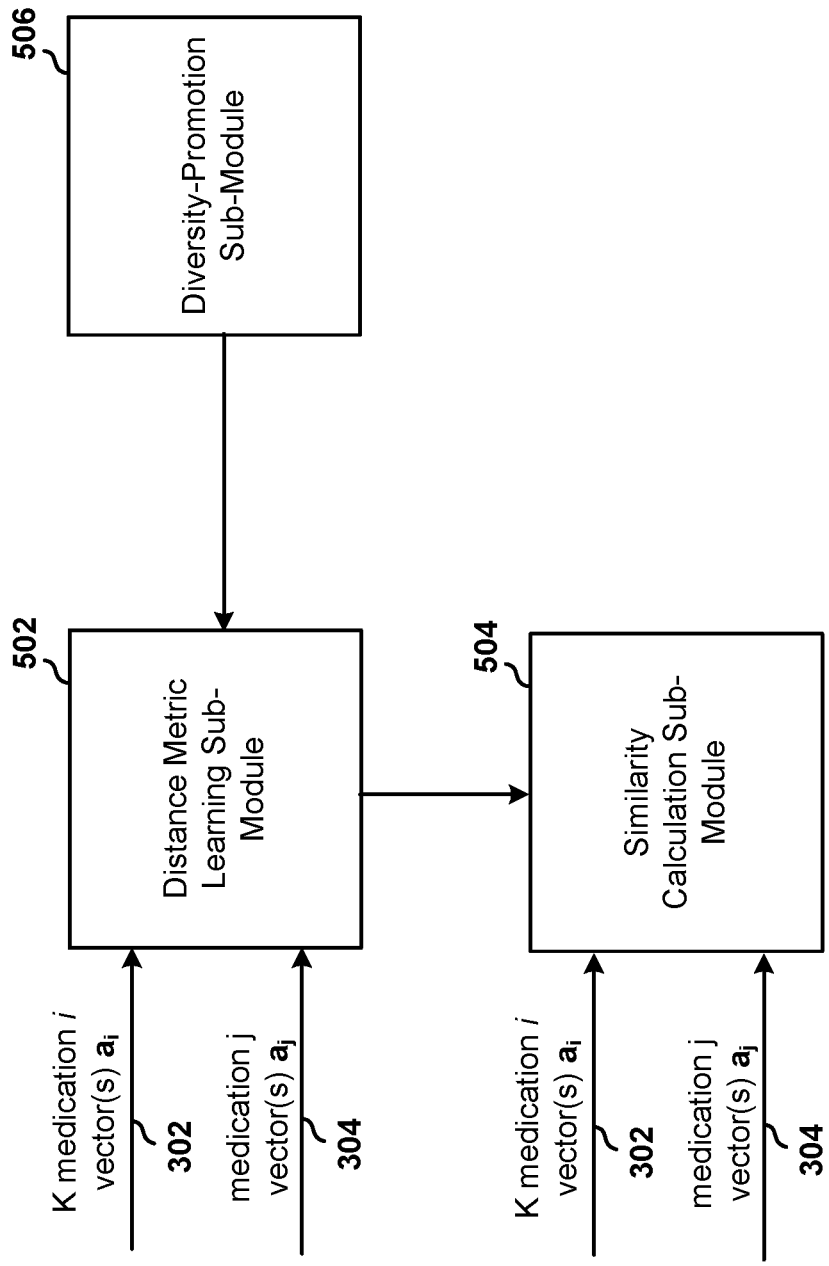
FIG. 5 is a detailed block diagram of a design for the medication correlation module of FIG. 4.

With reference to FIG. 4, the machine-learned algorithm 110b of FIG. 3 includes a medication correlation module 402 and a medication note dependency module 406. Collectively, these modules 402, 406 present a machine-learned algorithm that is designed to simultaneously model correlations among medications i and j and model dependencies between patient information and medications.

In one embodiment, the medication correlation module 402 implements a determinantal point process (DPP) that captures the correlations among the medications and outputs scalar measures 404 indicating the correlation of a medication i and a medication j. For example, given a set of medications each represented with a vector $a_i$ or $a_j$, the DPP computes a kernel matrix $L \in R^{K \times K}$, where $L_{ij}=k(a_i, a_j)$ and $k(\bullet,\bullet)$ is a kernel function to defines a probability distribution over subsets. Then the probability over a subset of items indexed by $S \subseteq \{1, \ldots, K\}$ can be defined as:

$$p(S) = \frac{\det(L_S)}{\det(L+I)} \quad \text{(Eq. 1)}$$

where
$L_S \equiv [L_{ij}]_{i,j \in S}$ denotes the restriction of L to the entries indexed by elements of S and
$\det(\bullet)$ denotes the determinant of a matrix and I is an identity matrix.

The determinant $\det(\bullet)$ enables the DPP to capture the high-order relations among items represented by the vectors $a_i$ and $a_j$. A DPP is applied to capture the correlation among medications: given the representations of K medications $\{a_i\}_{i=1}^K$, the kernel matrix L is computed and probability defined over medication-subset according to Eq. 1.

The medication note dependency module 406 incorporates a score function $g(a_i, x)$, which is derived as described above, into a kernel function in the DPP. On top of the kernel function $k(a_i, a_j)$ measuring the correlation between medication i and j, a new kernel is defined that is conditioned on the clinical information input x that is included in the score function $g(a_i,x)$:

$$\tilde{k}(a_i,a_j|x)=g(a_i,x)k(a_i,a_j)g(a_j,x) \quad \text{(Eq. 2)}$$

Under this conditional kernel parameterized by deep networks, a deep conditional DPP is obtained:

$$p(S|x) = \frac{\det(\tilde{L}_S(x))}{\det(\tilde{L}(x)+I)} \quad \text{(Eq. 3)}$$

where $\tilde{L}_{ij}(x)=\tilde{k}(a_i,a_j|x)$.

The deep conditional DPP is trained into the machine-learned algorithm 110b using historical information collected across a diverse patient population. Given training data $\{(d_n,S_n)\}_{n=1}^N$ where $d_n$ is a clinical information input record and $S_n$ is the subset of medications prescribed at discharge time, the parameters $\Theta$ of the deep conditional DPP, mainly the weight and bias parameters in DNNs, are learned by maximizing the data likelihood $$\max_\Theta L(\{(d_n,S_n)\}_{n=1}^N)=\Pi_{n=1}^N p(S_n|d_n;\Theta) \quad \text{(Eq. 4)}$$

Medical professionals have accumulated rich knowledge regarding the interactions between medications. These interactions largely affect the usage of medications. Specifically, two types of interactions are considered: antagonism and synergy. The antagonism interaction indicates that when used together, two medications may bring in a negative medical effect. Medications with antagonism interactions should be prohibited from being used together. The synergy interaction suggests that two medications are frequently used simultaneously to treat a disease. Their co-occurrence would bring in a positive medical effect and should be encouraged.

In another embodiment, a relational regularization model is designed and trained into the machine-learned algorithm 110b such that medications with synergy interaction are encouraged to be co-selected and those with antagonism interaction are penalized for co-selection. The relational regularization model is designed according to the property of DPP, which assigns larger probability mass p(S) over a medication subset S where the medications are more mutually "different". The "difference" between a medication i and a medication j, as presented by a respective medication i vector $a_i$ and a medication j vector $a_j$ is measured by the kernel function $k(a_i, a_j)$: the smaller $k(a_i, a_j)$ is, the more different the vectors $a_i$ and $a_j$ are, hence, the more different the medications are. To encourage medication i and j to be simultaneously selected into S, the relational regularization model encourages $k(a_i, a_j)$ to be small to increase p(S).

To discourage simultaneous selection, $k(a_i, a_j)$ is preferred to be large to decrease p(S). Denoting M and C the set of medication pairs possessing antagonistic and synergistic interactions respectively, the following relational regularization deep conditional DPP problem is defined $$\max_{\Theta} L(\{(d_n, S_n)\}_{n=1}^N) + \lambda(-\Sigma_{(i,j) \in M} k(a_i, a_j) + \Sigma_{(i,j) \in C} k(a_i, a_j)) \quad (6.5)$$

In the second term of the objective function, a medication pair (i, j) with synergistic interaction is encouraged to have smaller $k(a_i, a_j)$, while those with an antagonistic interaction are encouraged to have larger $k(a_i, a_j)$.

A machine-learned algorithm 110b designed and trained in accordance with the foregoing relational regularization deep conditional DPP performs well on frequent medications but less well on infrequent medications. To address this, in an alternate configuration, a diversity-promoting regularization may be applied to the medication correlation aspect of the machine-learned algorithm 110b to improve the algorithm's performance with respect to infrequent medications.

In this embodiment, medication i vectors a 302 and medication j vectors 304 are input to the distance metric learning sub-module 502 to learn a distance metric. The distance metric is featured by a projection matrix where the row vectors of this matrix project the representation vectors of the medications into a lower-dimensional latent space. For example, "diversity" may be characterized by considering two factors: uncorrelation and evenness. In this way, uncorrelation may be a measure of how uncorrelated components are. That is, less correlation is equivalent to more diversity. Additionally, for evenness in latent space modeling, components may play substantially equally important roles and no one component dominating, such that each component contributes significantly in data modeling.

In some embodiments, uncorrelation among components may be characterized from a statistical perspective by treating components as random variables and measuring their covariance which is proportional to their correlation. In one embodiment, $A \in \mathbb{R}^{d \times m}$ denotes the component matrix whose k-th column is the parameter vector $a_k$ of component k. In some embodiments, a row view of A: may be used where each component is treated as a random variable and each row vector $\tilde{a}_i^T$ is a sample drawn from the random vector formed by the m components. Further, $$\mu = \frac{1}{d}\sum_{i=1}^{d} \tilde{a}_i = \frac{1}{d} A^T 1$$

may be set as the sample mean, where the elements of $1 \in \mathbb{R}^d$ are all 1. An empirical covariance matrix may then be computed with the components as $$G = \frac{1}{d}\sum_{i=1}^{d}(\tilde{a}_i - \mu)(\tilde{a}_i - \mu)^T = \frac{1}{d} A^T A - \left(\frac{1}{d} A^T 1\right)\left(\frac{1}{d} A^T 1\right)^T.$$

By imposing the constraint $A^T 1 = 0$, therefore $$G = \frac{1}{d} A^T A.$$

Suppose A is a full rank matrix and m>d, then G is a full-rank matrix with rank m.

For the next step, the eigenvalues of G play important roles in characterizing the uncorrelation and evenness of components. Let $G = \Sigma_{k=1}^{m} \lambda_k u_k u_k^T$ be the eigendecomposition where $\lambda_k$ is an eigenvalue and $u_k$ is the associated eigenvector. In principle component analysis, an eigenvector $u_k$ of the covariance matrix G represents a principal direction of the data points and the associated eigenvalue $\lambda_k$ tells the variability of points along that direction. The larger $\lambda_k$ is, the more spread out the points along the direction $u_k$. When the eigenvectors (principal directions) are not aligned with the coordinate axis, the level of disparity among eigenvalues indicates the level of correlation among the m components (random variables). The more different the eigenvalues are, the higher the correlation is. Considering this, the uniformity among eigenvalues of G can be utilized to measure how uncorrelated the components are.

Secondly, the eigenvalues are related with the other factor of diversity: evenness. When the eigenvectors are aligned with the coordinate axis, the components are uncorrelated. In this case, evenness is used to measure diversity. In this example, each component is assigned an importance score. Since the eigenvectors are in parallel to the coordinate axis, the eigenvalues reflect the variance of components. Analogous to principle component analysis which posits that random variables with larger variance are more important, the present embodiment may use variance to measure importance. According to the evenness criteria, the components are more diverse if their importance scores match, which motivates us to encourage the eigenvalues to be uniform.

To sum up, the eigenvalues are encouraged to be even in both cases: (1) when the eigenvectors are not aligned with the coordinate axis, they are preferred to be even to reduce the correlation of components; (2) when the eigenvectors are aligned with the coordinate axis, they are encouraged to be even such that different components contribute equally in modeling data.

The similarity (or distance) of medications is then defined in the latent space. Further, row vectors of the projection matrix are encouraged to be diverse by a diversity-promotion sub-module. In some embodiments, by promoting diversity the row vectors evenly spread out and to represent both frequent medications and infrequent medications. By doing this, the similarity of infrequent medications can be better measured as the distance learning model counters skew toward frequent medications. The learned distance metric determined by the distance metric learning sub-module 502 and the medication i vectors $a_i$ 302 and medication j vectors 304 are input to the similarity calculation sub-module 504 to calculate the similarity score between the two medications.

In some embodiments, the distance metric learning sub-module 502 learns a distance metric. It takes representation vectors of two medications as inputs and produces a distance metric that can be utilized to measure the similarity of two medications. The distance metric between two medications is defined in the following way: given the representations of the medication's medication record, a linear projection matrix is utilized to project these representations into a latent space; then the squared Euclidean distance between the latent representations is measured. The distance metric learning sub-module learns this distance metric (specifically, the linear projection matrix) by encouraging the distance between similar medications to be as small as possible, and encouraging the distance between dissimilar medications to be separated by a margin.

A diversity-promotion sub-module 506 is utilized to control the row vectors of the distance matrix in the distance metric learning sub-module 502, such that these vectors are diverse. In this embodiment, by promoting diversity the row vectors spread out and give frequent medications and infrequent medications a fair treatment. In this way, the similarity among infrequent medications and frequent medications can be better measured. Diversity is measured using near-orthogonality: vectors that are close to being orthogonal are more diverse. To encourage near-orthogonality, the diversity-promotion sub-module 506 computes the Gram matrix of the row vectors, then encourages the Gram matrix to be close to an identity matrix where the closeness is measured using Bregman matrix divergence.

The similarity calculation sub-module 504 calculates the similarity of two medications. It takes the representation vectors, i.e., the medication i vectors $a_i$ 302 and medication j vectors 304, as input and produces a score that indicates the similarity of the two medications. At the core of this sub-module 504 is a distance matrix (learned by the DML sub-module) where the row vectors of this matrix project the representation vectors of the medications into a lower-dimensional latent space. The similarity of medications is then measured in the latent space.

In some embodiments, to promote uniformity among eigenvalues, as a general approach, eigenvalues may be normalized into a probability simplex and then the discrete distribution parameterized by the normalized eigenvalues may be encouraged to have small Kullback-Leibler (KL) divergence with the uniform distribution. Given the eigenvalues $\{\lambda_k\}_{k=1}^m$, they are then normalized into a probability simplex $$\hat{\lambda}_k = \frac{\lambda_k}{\sum_{j=1}^m \lambda_k}$$

based on which a distribution is defined on a discrete random variable $X=1, \ldots, m$ where $p(X=k)=\hat{\lambda}_k$.

In addition, to ensure the eigenvalues are strictly positive, $A^T A$ may be set to be positive definite. To encourage $\{\lambda_k\}_{k=1}^m$ to be uniform, the distribution $p(X)$ is set be "close" to a uniform distribution $$q(X=k) = \frac{1}{m},$$

where the "closeness" is measured using KL divergence $$KL(p \| q): \sum_{k=1}^m \hat{\lambda}_k \log \frac{\lambda_k}{1/m} = \frac{\sum_{k=1}^m \lambda_k \log \lambda_k}{\sum_{j=1}^m \lambda_j} - \log \sum_{j=1}^m \lambda_j + \log m.$$

In this equation, $\Sigma_{k=1}^m \lambda_k \log \lambda_k$ is equivalent to $$tr\left(\left(\frac{1}{d}A^T A\right)\log\left(\frac{1}{d}A^T A\right)\right),$$

where log(•) denotes matrix logarithm. To show this, note that $$\log\left(\frac{1}{d}A^T A\right) = \sum_{k=1}^m \log(\lambda_k) u_k u_k^T,$$

according to the property of matrix logarithm. Then, $$tr\left(\left(\frac{1}{d}A^T A\right)\log\left(\frac{1}{d}A^T A\right)\right)$$

is equal to $tr((\Sigma_{k=1}^m \lambda_k u_k u_k^T)(\Sigma_{k=1}^m \log(\lambda)k\ u_k u_k^T))$ which equals to $\Sigma_{k=1}^m \lambda_k \log \lambda_k$. According to the property of trace, $$tr\left(\frac{1}{d}A^T A\right) = \sum_{k=1}^m \lambda_k.$$

then the KL divergence can be turned into a diversity-promoting uniform eigenvalue regularizer (UER):

$$\frac{tr\left(\left(\frac{1}{d}A^T A\right)\log\left(\frac{1}{d}A^T A\right)\right)}{tr\left(\frac{1}{d}A^T A\right)} - \log tr\left(\frac{1}{d}A^T A\right),$$

subject to $A^T A \succ 0$ and $A^T 1 = 0$.

UER then may be applied to promote diversity. For example, let $\mathcal{L}(A)$ denote the objective function of an ML model, then a UE-regularized ML problem can be defined as $$\min_A \mathcal{L}(A) + \lambda \left(\frac{tr\left(\left(\frac{1}{d}A^T A\right)\log\left(\frac{1}{d}A^T A\right)\right)}{tr\left(\frac{1}{d}A^T A\right)} - \log tr\left(\frac{1}{d}A^T A\right)\right)$$

subject to $A^T A \succ 0$ and $A^T 1 = 0$, where $\lambda$ is the regularization parameter.

Uniform eigenvalue regularizers may then be applied to promote diversity in a specific model: distance metric learning (DML). Given data pairs either labeled as "similar" or "dissimilar", distance metric learning aims to learn a distance metric under which similar pairs would be placed close to each other and dissimilar pairs are separated apart. The learned distance can benefit a wide range of tasks, including retrieval, clustering and classification. The distance metric may be defined as between x, $y \in \mathbb{R}_d$ as $\|A^T x - A^T y\|_2^2$ where $A \in \mathbb{R}^{d \times m}$ is a parameter matrix whose column vectors are components. A uniform eigenvalue regularized DML (UE-DML) problem can then be formulated as:

$$\min_A \sum_{(x,y)\in \mathcal{S}} \|A^T x - A^T y\|_2^2 + \sum_{(x,y)\in \mathcal{D}} \max(0, 1 - \|A^T x - A^T y\|_2^2) +$$

$$\lambda \left( \frac{tr\left(\left(\frac{1}{d}A^T A\right)\log\left(\frac{1}{d}A^T A\right)\right)}{tr\left(\frac{1}{d}A^T A\right)} - \log tr\left(\frac{1}{d}A^T A\right) \right)$$

subject to $A^T A \succ 0$ and $A^T 1 = 0$, where $\mathcal{S}$ and $\mathcal{D}$ are the set of similar and dissimilar pairs respectively. The first and second term in the objective function encourage similar pairs to have small distances and dissimilar pairs to have large distances respectively.

The UE regularizer is nonconvex and is difficult to be convexified. As a result, the UE-regularized ML problems are nonconvex where achieving the global optimal is NP-hard. In this section, diversity-promoting regularizers are designed that make convex relaxation easier. Nonconvex regularizers are defined based on Bregman matrix divergence, then discuss how to convexify them.

Diversity may also be defined as near-orthogonality, wherein component vectors are determined to be more diverse if they are closer to being orthogonal. To encourage near orthogonality between two vectors $a_i$ and $a_j$, one way is to make their inner product $a_i^T a_j$ close to zero and their $l_2$ norm $\|a_i\|_2$, $\|a_j\|_2$ close to one. For a set of vectors $\{a_i\}_{i=1}^m$, near orthogonality can be achieved in the following manner by computing the Gram matrix G where $G_{ij} = a_i^T a_j$, then encouraging G to be close to an identity matrix. Off the diagonal of G and I are $a_i^T a_j$ and zero respectively. On the diagonal of G and I are $\|a_i\|_2^2$ and one respectively. Making G close to I effectively encourages $a_i^T a_j$ to be close to zero and $\|a_i\|_2$ close to one, which therefore encourages $a_i$ and $a_j$ to get close to orthogonal.

A Bregman matrix divergence (BMD) may be used to measure "closeness" between two matrices. Let $\mathcal{S}^n$ denote real symmetric n×n matrices. Given a strictly convex, differentiable function $\phi: \mathcal{S}^n \to \mathbb{R}$, the BMD is defined as $D_\phi(X, Y) = \phi(X) - \phi(Y) - tr((\nabla\phi(Y))^T (X-Y))$, where $tr(A)$ denotes the trace of matrix A. Different choices of $\phi(X)$ lead to different divergences. When $\phi(X) = \|X f_F^2$, BMD is specialized to the squared Frobenius norm (SFN) $\|X-Y\|_F^2$. If $\phi(X) = tr(X \log X - X)$, where $\log X$ denotes the matrix logarithm of X, the divergence becomes $D_{vN}(X, Y) = tr(X \log X - X \log Y - X + Y)$, which is von Neumann divergence (VND). If $\phi(X) = -\log \det X$ where $\det(X)$ denotes the determinant of X, the log-determinant divergence (LDD) $D_{lD}(X, Y) = tr(XY^{-1}) - \log \det(XY^{-1}) - n$.

To encourage near-orthogonality among components, the BMD between the Gram matrix $AA^T$ and an identity matrix I may be small, which results in a family of BMD regularizers: $\Omega_\phi(A) = D_\phi(AA^T, I)$. $\Omega_\phi(A)$ can be specialized to different instances, according to the choices of $D_\phi(\cdot,\cdot)$. Under SFN, $\Omega_\phi(A)$ becomes $\Omega_{Fro}(A) = \|AA^T - I\|_F^2$. Under VND, $\Omega_\phi(A)$ becomes $\Omega_{vN}(A) = tr(AA^T \log(AA^T) - AA^T) + m$. Under LDD, $\Omega_\phi(A)$ becomes $\Omega_{ld}(A) = tr(AA^T) - \log \det(AA^T) - m$.

Applying these regularizers to distance metric learning (DML), the following BMD-regularized DML (BMD-DML) problem is defined as:

$$\min_A \frac{1}{|\mathcal{S}|} \sum_{(x,y)\in \mathcal{S}} \|Ax - Ay\|_2^2 + \frac{1}{|\mathcal{D}|} \sum_{(x,y)\in \mathcal{D}} \max(0, 1 - \|Ax - Ay\|_2^2) + \lambda \Omega_{\phi(A)}$$

which is nonconvex.

Figure 6:
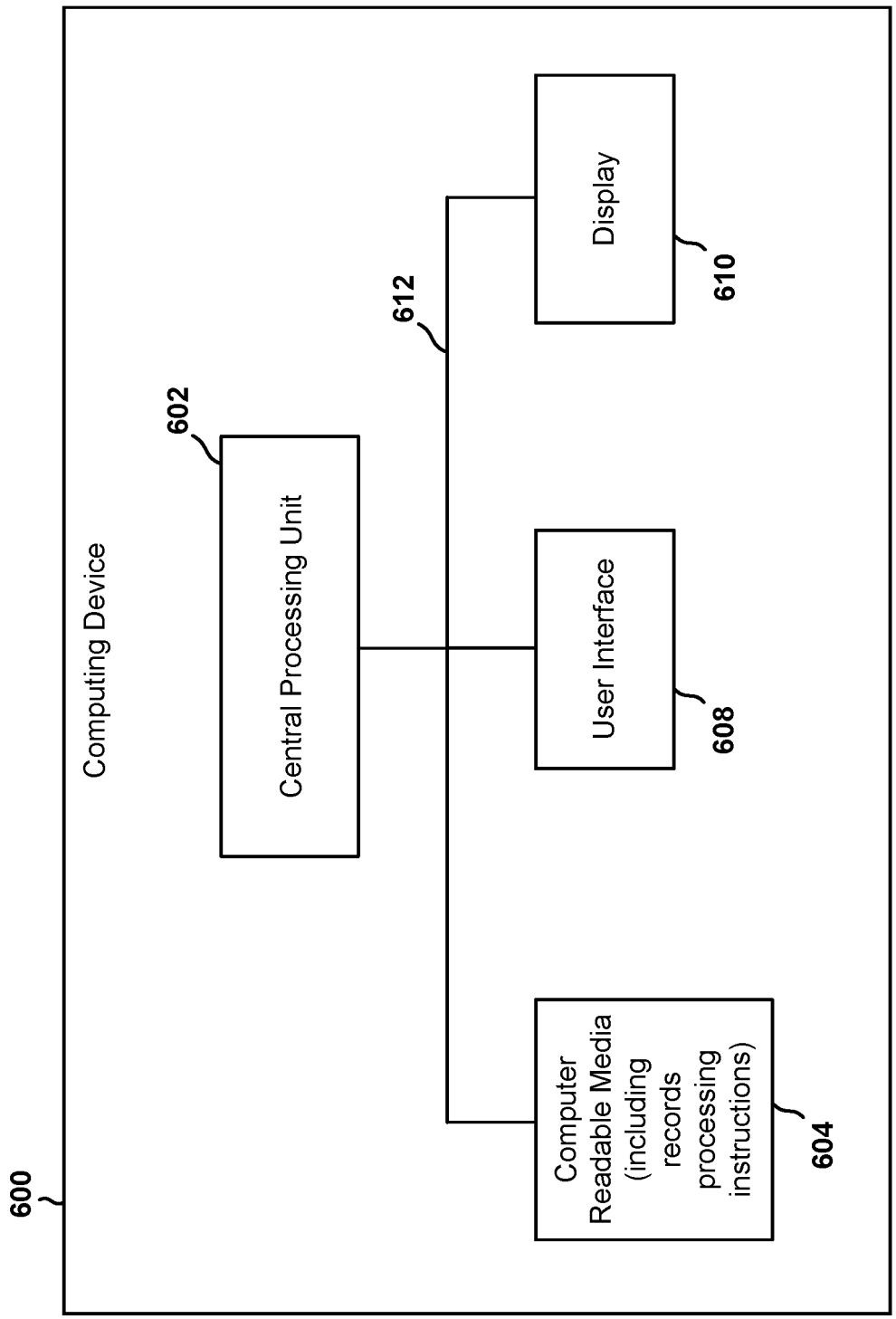
FIG. 6 is a block diagram of a computing device that embodies the system of FIG. 1.

FIG. 6 is a block diagram of a computing device 600 that embodies the medication prediction system of FIG. 1. The computing device 600 is specially configured to execute instructions related to the medication prediction processing described above, including the application of machine-learned algorithms to clinical information records. Computers capable of being specially configured to execute such instructions may be in the form of a laptop, desktop, workstation, or other appropriate computer capable of connecting to the medication prediction system 100 of FIG. 1.

The computing device 600 includes a central processing unit (CPU) 602 that implements the various modules of the medication prediction system 100 described above with reference to FIG. 1, and a computer readable media 604 that includes program instructions that enable the CPU to implement the modules of the medication prediction system 100. The computing device 600 also includes a user interface 608 and a display 610, and an interface bus 612 that interconnects all components of the computing device.

Computer readable media 604 suitable for storing medication prediction system processing instructions include all forms of non-volatile memory, media and memory devices, including by way of example semiconductor memory devices, flash memory devices, magnetic disks, magneto optical disks and CD ROM and DVD-ROM disks. In operation, the CPU 602 executes the medication prediction system processing instructions stored in the computer readable media 604 to thereby perform the functions of the text encoding module 102 and the medication prediction module 104.

The user interface 608, which may be a keyboard or a mouse, and the display 610 allow for a clinician to interface with the computing device 600 and the components of the medication prediction system 100. For example, a clinician seeking to obtain a set of medications to prescribe to a subject patient, may input a record or a number of input records of a subject patient for processing. The clinician may then initiate execution of the medication prediction system processing instructions stored in the computer readable media 604 through the user interface 608, and await a display of the predicted medications.

While various embodiments have been described above, they have been presented by way of example only, and not by way of limitation. Likewise, the various diagrams may depict an example architectural or other configuration for the disclosure, which is done to aid in understanding the features and functionality that can be included in the disclosure. The disclosure is not restricted to the illustrated example architectures or configurations, but can be implemented using a variety of alternative architectures and configurations.

In this document, the terms "module" and "engine" as used herein, refers to software, firmware, hardware, and any combination of these elements for performing the associated functions described herein. Additionally, for purpose of discussion, the various modules are described as discrete modules; however, as would be apparent to one of ordinary skill in the art, two or more modules may be combined to form a single module that performs the associated functions according embodiments of the invention.

In this document, the terms "computer program product", "computer-readable medium", and the like, may be used generally to refer to media such as, memory storage devices, or storage unit. These, and other forms of computer-readable media, may be involved in storing one or more instructions for use by processor to cause the processor to perform specified operations. Such instructions, generally referred to as "computer program code" (which may be grouped in the form of computer programs or other groupings), when executed, enable the computing system.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; and adjectives such as "conventional," "traditional," "normal," "standard," "known", and terms of similar meaning, should not be construed as limiting the item described to a given time period, or to an item available as of a given time. But instead these terms should be read to encompass conventional, traditional, normal, or standard technologies that may be available, known now, or at any time in the future.

Additionally, memory or other storage, as well as communication components, may be employed in embodiments of the invention. It will be appreciated that, for clarity purposes, the above description has described embodiments of the invention with reference to different functional units and processors. However, it will be apparent that any suitable distribution of functionality between different functional units, processing logic elements or domains may be used without detracting from the invention. For example, functionality illustrated to be performed by separate processing logic elements or controllers may be performed by the same processing logic element or controller. Hence, references to specific functional units are only to be seen as references to suitable means for providing the described functionality, rather than indicative of a strict logical or physical structure or organization.

Furthermore, although individually listed, a plurality of means, elements or method steps may be implemented by, for example, a single unit or processing logic element. Additionally, although individual features may be included in different claims, these may possibly be advantageously combined. The inclusion in different claims does not imply that a combination of features is not feasible and/or advantageous. Also, the inclusion of a feature in one category of claims does not imply a limitation to this category, but rather the feature may be equally applicable to other claim categories, as appropriate.

The various aspects of this disclosure are provided to enable one of ordinary skill in the art to practice the present invention. Various modifications to exemplary embodiments presented throughout this disclosure will be readily apparent to those skilled in the art. Thus, the claims are not intended to be limited to the various aspects of this disclosure, but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

What is claimed is:

1. A method of predicting medications to prescribe to a patient, the method comprising:
    obtaining, by one or more processors, a clinical-information vector from clinical information of the patient; and
    applying, by the one or more processors, a machine-learned medication-prediction algorithm to the clinical-information vector to select a subset of medications to prescribe to the patient, wherein applying a medication-prediction algorithm to the clinical-information vector comprises, for each medication in a set of medications:
        determining a score function comprises obtaining a measure of correlation between the patient's clinical information and the medication; and
        including the medication in the subset of medications if the score function satisfies a criterion,
        wherein the medications included in the subset of medications to prescribe to the patient are selected from a first set of medications i and a second set of medications j, and determining a score function comprises obtaining a measure of correlation between a medication in the first set of medications and a medication in the second set of medications, wherein obtaining a measure of correlation comprises calculating uncorrelation between representation vectors of a first set of medications i and a second set of medications j, wherein uncorrelation is calculated using eigenvalues of component matrices composed from representation vectors of a first set of medications i and a second set of medications j, wherein uniformity among the eigenvalues measures uncorrelation between components.

2. The method of claim 1, wherein determining a score function comprises implementing a determinantal point process to obtain the measure of correlation.

3. The method of claim 2, wherein determining a score function further comprises implementing a deep conditional determinantal point process to obtain a measure of dependency between a clinical condition and a pair of correlated medications.

4. The method of claim 2, wherein determining a score function further comprises implementing a relation-regularized deep conditional determinantal point process to obtain a measure of dependency between a clinical condition and a pair of correlated medications, wherein the correlation among medications accounts for synergistic and antagonistic interactions.

5. The method of claim 2, wherein determining a score function further comprises implementing a diversity-promoting regularization model.

6. The method of claim 1, wherein obtaining a measure of correlation comprises calculating a distance metric using a projection matrix, where the row vectors of the projection matrix project representation vectors of a first set of medications i and a second set of medications j into a lower-dimensional latent space.

7. The method of claim 1, wherein eigenvalues are promoted to be uniform in order to promote evenness between components.

8. The method of claim 1, further including normalizing the eigenvalues into a probability simplex and encouraging the discrete distribution parameterized by the normalized eigenvalues to have small Kullback-Leibler (KL) divergence with the uniform distribution.

9. The method of claim 8, further comprising calculating a distance metric based on similarity between the normalized eigenvalues between the representation vectors of a first set of medications i and a second set of medications j.

10. The method of claim 1, wherein the row vectors are encouraged to be near-orthogonal to promote diversity between the components.

11. A system predicting medications to prescribe to a patient, the system comprising:
a processor configured for:
obtaining a clinical-information vector from clinical information of the patient; and
applying a machine-learned medication-prediction algorithm to the clinical-information vector to select a subset of medications to prescribe to the patient, wherein applying the machine-learned medication-prediction algorithm to the clinical-information vector comprises, for each medication in a set of medications:
determining a score function comprises obtaining a measure of correlation between the patient's clinical information and the medication; and
including the medication in the subset of medications if the score function satisfies a criterion, wherein the medications included in the subset of medications to prescribe to the patient are selected from a first set of medications i and a second set of medications j, and determining a score function comprises obtaining a measure of correlation between a medication in the first set of medications and a medication in the second set of medications, wherein obtaining a measure of correlation comprises calculating uncorrelation between representation vectors of a first set of medications i and a second set of medications j, wherein uncorrelation is calculated using eigenvalues of component matrices composed from representation vectors of a first set of medications i and a second set of medications j, wherein uniformity among the eigenvalues measures uncorrelation between components.

* * * * *